United States Patent [19]

Jacobson et al.

[11] Patent Number: 5,200,493

[45] Date of Patent: Apr. 6, 1993

[54] HETEROATOM CONTAINING PERFLUORALKYL TERMINATED NEOPENTYL MERCAPTO-ALCOHOLS AND COMPOSITIONS THEREFROM

[75] Inventors: Michael Jacobson, Haworth, N.J.; Kirtland P. Clark, Bethel, Conn.

[73] Assignee: Ciba-Geigy Corporation, Ardsley, N.Y.

[21] Appl. No.: 901,488

[22] Filed: Jun. 19, 1992

Related U.S. Application Data

[60] Division of Ser. No. 660,603, Feb. 25, 1991, Pat. No. 5,145,996, which is a continuation-in-part of Ser. No. 620,232, Nov. 29, 1990, Pat. No. 5,097,067, which is a continuation-in-part of Ser. No. 444,073, Nov. 30, 1989, Pat. No. 5,097,048.

[51] Int. Cl.$^5$ .............................................. C08G 18/38
[52] U.S. Cl. .................................... 528/70; 528/60
[58] Field of Search ................................ 528/70, 60

[56] References Cited

U.S. PATENT DOCUMENTS 3,886,201  5/1975  Falk ...................................... 260/481

FOREIGN PATENT DOCUMENTS 0348350  12/1989  European Pat. Off. .
0376882   7/1990  European Pat. Off. .
0430887   6/1991  European Pat. Off. .
0453406  10/1991  European Pat. Off. .

*Primary Examiner*—Maurice J. Welsh
*Attorney, Agent, or Firm*—Kevin T. Mansfield; Edward McC. Roberts

[57] ABSTRACT

Heteroatom containing perfluoroalkyl terminated neopentyl mercapto-alcohols of the formulas I and II $$HS-[CH_2C(CH_2X-E-R_f)_2CH_2]-OH \qquad (I)$$

$$HS-[CH_2C(CH_2X_1-R_f)_2CH_2]-OH \qquad (II)$$

are prepared from the corresponding perfluorinated neopentyl oxetanes where $R_f$ is a straight or branched chain perfluoroalkyl of 1 to 18 carbon atoms or said perfluoroalkyl substituted by perfluoroalkoxy of 2 to 6 carbon atoms, E is a linking group, and X and $X_1$ are heteroatom moieties.

The reaction products of these fluorinated mercapto-alcohols with electrophiles are disclosed as are certain functional derivatives. Compositions containing such materials provide improved thermal stability and useful low surface energy oil and water repellent coatings for textiles, glass, paper, leather, and other materials.

7 Claims, No Drawings

HETEROATOM CONTAINING PERFLUORALKYL TERMINATED NEOPENTYL MERCAPTO-ALCOHOLS AND COMPOSITIONS THEREFROM

This is a divisional of Ser. No. 660,603, filed Feb. 25, 1991, now U.S. Pat. No. 5,145,996 which is a continuation-in-part of application Ser. No. 620,232, filed on Nov. 29, 1990, now U.S. Pat. No. 5,097,067, which is in turn a continuation-in-part of application Ser. No. 444,073, filed on Nov. 30, 1989, now U.S. Pat. No. 5,097,048.

BACKGROUND OF THE INVENTION

This invention relates to novel hetero group containing perfluoroalkyl terminated neopentyl mercapto-alcohols which possess improved thermal stability. They are useful in the preparation of low surface energy oil and water repellent coatings for textiles, glass, paper, leather, and other materials.

One other bis-perfluoroalkyl terminated mercaptan has been previously described in U.S. Pat. Nos. 3,758,447 and 3,886,201 and Japanese Sho 63-223,639. However, this compound is a perfluoroalkyl ester of mercaptosuccinic acid and is not only expensive to prepare, but also is not thermally and hydrolytically stable. Therefore, it is an impractical intermediate from which to obtain useful products.

The instant twin-$R_f$ tailed mercapto-alcohols are readily isolated in high yield and purity. In addition, because of the neopentyl skeleton is incorporated into all of the novel mercapto-alcohols, they are thermally stable as well.

Bis-perfluoroalkyl mercapto-alcohols and derivatives thereof are useful because they possess a low free surface energy which provides oil and water repellency to a wide variety of substrates. Mercaptans containing a single $R_f$-function are known, but do not provide these properties to the same extent. The proximity of the two perfluoroalkyl chains to one another greatly increases the attraction between these groups through Van Der Waal's interactive forces, and as a result the oil and water repellency of the twin-tailed mercaptans is much greater than the repellency inherent in single-tailed mercaptans.

OBJECTS OF THE INVENTION

This invention most generally relates to novel heteroatom containing perfluoroalkyl terminated neopentyl mercapto-alcohols and compositions derived therefrom.

This invention also relates to the reaction products of said mercaptans with electrophiles. Other aspects of this invention are the derivatization of the alcohols as esters or urethanes. The products are useful per se or as intermediates for coatings on textiles, glass, linoleum, leather, wood, tile, metals, plastics and other various materials.

Another aspect of this invention relates to a substrate containing 0.01 to 50% by weight of a fluorine-containing mercapto-alcohol composition, at least part of said fluorine being provided by one unit derived from a heteroatom containing $R_f$-neopentyl mercapto-alcohol.

DETAILED DISCLOSURE

The instant invention pertains to novel heteroatom containing $R_f$-neopentyl mercapto-alcohols of formula I or II

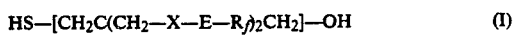

wherein
$R_f$ is a straight or branched chain perfluoroalkyl of 1 to 18 carbon atoms or said perfluoroalkyl substituted by perfluoroalkoxy of 2 to 6 carbon atoms,
E is branched or straight chain alkylene of 1 to 10 carbon atoms or said alkylene interrupted by one to three groups selected from the group consisting of —NR—, —O—, —S—, $SO_2$—, —COO—, —OOC—, —CONR—, —NRCO—, —$SO_2$NR—, and —NR$SO_2$—, or terminated at the $R_f$ end with —CONR— or —$SO_2$NR—, where $R_f$ is attached to the carbon or sulfur atom,
X is —S—, —O—, —$SO_2$—, or —NR—,
$X_1$ is —CONR— or —$SO_2$NR—, where $R_f$ is attached to the carbon or sulfur atom, and
where R is independently hydrogen, alkyl of 1 to 6 carbon atoms or hydroxyalkyl of 2 to 6 carbon atoms.

It is understood that the $R_f$ group usually represents a mixture of perfluoroalkyl moieties. When the $R_f$ group is identified as having a certain number of carbon atoms, the said $R_f$ group also usually concomitantly contains a small fraction of perfluoroalkyl groups with a lower number of carbon atoms and a small fraction of perfluoroalkyl groups with a higher number of carbon atoms.

Preferably the instant compounds of formula I or II are those where $R_f$ is perfluoroalkyl of 4 to 18 carbon atoms or perfluoroalkyl of 2 to 6 carbon atoms substituted by perfluoroalkoxy of 2 to 6 carbon atoms.

Preferably the instant compounds of formula I are those where $R_f$ is perfluoroalkyl of 6 to 16 carbon atoms or perfluoroalkyl of 2 to 6 carbon atoms substituted by perfluoroalkoxy of 2 to 6 carbon atoms, E is alkylene of 2 to 6 carbon atoms, —CONHCH$_2$CH$_2$—, —CH$_2$CH$_2$N(CH$_3$)CH$_2$CH$_2$—, —CH$_2$CH$_2$SO$_2$NHCH$_2$CH$_2$—, —CH$_2$CH$_2$OCH$_2$CH$_2$—, or —SO$_2$NHCH$_2$CH$_2$—, and X is —S—, —$SO_2$— or —O—.

Most preferred are those compounds where $R_f$ is perfluoroalkyl of 6 to 14 carbon atoms, E is ethylene, and X is S, i.e., ($R_f$CH$_2$CH$_2$SCH$_2$)$_2$C(CH$_2$OH)(CH$_2$SH).

The novel $R_f$-mercapto-alcohols can be obtained directly by the reaction of a sulfur containing reagent with a bis-perfluoroalkyl oxetane of formula III or IV

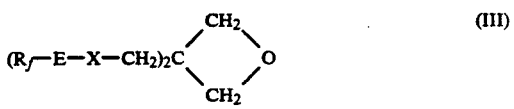

or

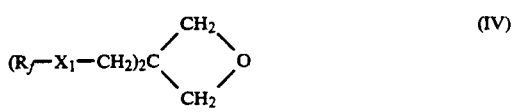

The above-identified oxetanes are described in co-pending patent application Ser. No. 444,073.

The synthesis of $R_f$-mercapto-alcohols proceeds by the nucleophilic addition of a sulfur containing reagent with the above-identified oxetane. This method of opening oxetanes to 3-mercapto-1-propanols has been previously described by Rondestvedt in the Journal of Organic Chemistry, 26, 3024 (1961). The reaction may be conducted in an aqueous system using phase transfer catalysis, but work-up of such an aqueous product is difficult due to troublesome emulsions. The improved process of this invention involves the combination of:

a. an organic solvent, such as N-methylpyrrolidone, N,N-dimethylformamide, dimethyl sulfoxide, or the like, or alcohols such as methanol, ethanol, isopropanol or tert-butanol, or ketones, such as acetone, methyl alkyl ketones, or dialkyl ketones. Chlorinated solvents and esters generally give poor conversions and are less suitable;

b. moderate reaction temperatures, on the order of 50° to about 120° C.; and c. a stoichiometric quantity of a sulfur containing reagent, preferably an alkaline earth metal salt of thiocyanate, xanthate, mercaptoacetic acid or a neutral sulfur containing reagent such as thiourea, in the ratio of 1 mole of sulfur reagent per mole of oxetane to be cleaved; and d. a non-nucleophilic acid catalyst as exemplified by sulfuric acid or perchloric acid.

The reaction temperature and choice of solvent are mutually dependent. A reaction temperature in the range of 50°-120° C. is one wherein the formation of undesirable by-products is minimized and wherein the reaction products are stable.

Conditions are adjusted in order to achieve a reasonable rate of reaction at the chosen temperature.

Another aspect of the instant invention is a product prepared from the instant mercapto-alcohol by reaction with various electrophiles.

The heteroatom containing perfluoroalkyl terminated oxetanes described in copending applications Ser. Nos. 444,073 and 620,232 are not only precursors for the instant mercapto-alcohols, but also for the corresponding halohydrins and dihalides. These latter materials as well as the instant mercapto-alcohols can be used to prepare compounds of the formula V or VI $$T_1-CH_2-C(CH_2-X-E-R_f)_2-CH_2-T_2 \quad (V)$$

$$T_1-CH_2-C(CH_2-X_1-R_f)_2-CH_2-T_2 \quad (VI)$$

where $T_1$ is the group VII $$-S-C(R_1)(R_3)-C(R_2)(R_4) \quad (VII)$$

where $R_1$, $R_2$, $R_3$ and $R_4$ are independently hydrogen, alkyl of 1 to 18 carbon atoms, hydroxyalkyl of 1 to 4 carbon atoms, haloalkyl of 1 to 4 carbon atoms, alkoxyalkyl of 2 to 12 carbon atoms, phenyl, phenyl substituted by one or two alkyl of 1 to 4 carbon atoms, by alkoxy of 1 to 4 carbon atoms, by carboxy or by hydroxy, phenylalkyl of 7 to 9 carbon atoms, carboxy, —COOZ where Z is alkyl of 1 to 18 carbon atoms, said alkyl interrupted by one or more —O— groups, allyl, cyclohexyl, phenyl, benzyl, tolyl or naphthyl; or —CONZ$_1$Z$_2$ where Z$_1$ and Z$_2$ are independently hydrogen, alkyl of 1 to 12 carbon atoms, hydroxyalkyl of 2 to 4 carbon atoms, phenyl, benzyl, alkoxyalkyl of 2 to 12 carbon atoms, cyclohexyl or Z$_1$ and Z$_2$ together are pentamethylene or 3-oxapentamethylene, with the proviso that at least one of $R_1$ to $R_4$ contains a carboxy, —COOZ or —CONZ$_1$Z$_2$ group, and $T_2$ has the same meaning as $T_1$ or is hydroxyl.

Preferably, one or both of $T_1$ and $T_2$ is a residue of a mercapto mono- or di-carboxylic acid of 2 to 4 carbon atoms after removal of the hydrogen atom from the mercapto group, and the other of $T_1$ and $T_2$ is hydroxyl.

Most preferably, both $T_1$ and $T_2$ are a residue of a mercapto mono- or di-carboxylic acid of 2 to 4 carbon atoms after removal of the hydrogen atom from the mercapto group; or $T_1$ is the residue of a mercapto mono- or di-carboxylic acid of 2 to 4 carbon atoms after removal of the hydrogen atom from the mercapto group, and $T_2$ is hydroxyl.

Preferably the mercapto acid is mercaptoacetic, thiolactic, 3-mercaptopropionic or mercaptosuccinic acid.

The compounds where $T_2$ is hydroxyl and $T_1$ is a group VII can also be made by the addition of the mercapto-alcohol to an activated ethylenically unsaturated double bond as discussed below.

Some products can be derived through base-catalyzed nucleophilic additions to electrophilic substrates. For example, the base catalyzed addition reaction of mercaptans to alpha,beta-unsaturated esters is well known and described in detail in: Houben-Weyl, Methoden der Organischen Chemie, Volume 9/4, pages 123 to 126 (George Thieme Verlag, Stuttgart, 1955). Likewise, the base-catalyzed addition reaction of mercaptans to other electrophilic substrates, e.g. halides, sulfonates, acetates, is well known and described in Houben-Weyl, Methoden der Organischen Chemie, vol. 9/4 (George Thieme Verlag, Stuttgart, 1955, pp. 97-147), Barton and Ollis, Comprehensive Organic Chemistry vol. 3 (Pergamon Press, Oxford, 1979, pp. 13-16) and M. E. Peach in Patai, S., The Chemistry of the Thiol Group Part 2 (John Wiley and Sons, New York, 1974, pp. 722-734).

The types of electrophilic groups and hence the compounds that may be employed in conjunction with the perfluoroalkyl ($R_f$) containing mercapto-alcohols are numerous. The sole criticality is that nucleophilic addition/substitution occurs. Therefore in the presence of the disclosed mercaptans, addition/substitution will take place and the moiety will be introduced as a constituent of the final product. The basic reaction of mercaptans of the formula RSH involving addition/substitution of electrophiles is considered well documented in the literature.

Electrophiles of interest are generally all electrophiles which can be efficiently reacted and can therefore be employed for the synthesis of adducts. Several excellent surveys of mercaptan reactions with electrophiles are described and reference was made above to these teachings. A desired class of electrophiles therefore can be considered to be those possessing ethylenic unsaturation and those which readily undergo nucleophilic substitution.

During the nucleophilic addition/substitution, the mercaptan derived moiety is introduced as an integral part of the molecule.

The class of unsaturated and other electrophilic compounds encompassed within the scope of this disclosure are those formed by compounds undergoing nucleophilic addition and contain the perfluoroalkyl moiety.

It is also possible to use free radical initiators or UV light for the addition of mercaptans to di- and triesters, as well as mono-esters and other nucleophilic substrates. This is possible because the di- and triesters are in contrast to acrylic esters, very reluctant to homopolymerize. A suitable catalyst may be any one of the commonly known agents for initiating the polymerization of vinyl monomers such as azo-initiators, (e.g., azobisisobutyronitrile) or aliphatic and aromatic acyl peroxides, e.g., decanoyl peroxide, lauroyl peroxide, benzoyl peroxide, dialkyl peroxides e.g., t-butyl peroxide, cumylperoxide; or hydroperoxides, e.g., t-butyl hydroperoxide, cumene hydroperoxide, or peresters and peroxycarbonates, e.g., t-butyl perbenzoate.

The addition of the mercaptans to the di- and triesters is usually carried out in a solvent in which the reactants and preferably also the adduct are soluble at the reaction temperature employed. Suitable solvents are aliphatic or aromatic hydrocarbons such as heptane, benzene, toluene, etc; chlorinated or fluorinated aliphatic or aromatic hydrocarbons such as methylene chloride, chloroform, methyl chloroform, carbon tetrachloride, trichloroethylene, perchloroethylene, FREON's such as 1,1,2-trifluoro-1,2,2-trichloroethane, etc., chlorobenzene, benzotrifluoride or hexafluoroxylene, ketones, esters and ethers such as acetone, methyl isobutyl ketone, ethyl acetate and higher homologs, dialkyl ethers, tetrahydrofuran, ethylene glycol monomethyl or monoethyl ether, ethylene glycol dimethyl or diethyl ether, and mixtures of these ketones, esters or ethers with water.

Non-ionic hydrophilic and hydrophobic activated olefins for such Michael reactions are known per se and many are commercially available, and include for example, but without limitation, alkyl acrylates and alkyl methacrylates, such as methyl methacrylate, ethyl methacrylate, isobutyl methacrylate, hexyl methacrylate, and n-octyl methacrylate. The esters of acrylic acids include methyl, ethyl, propyl, butyl, 2-hydroxyethyl, 3-hydroxypropyl, 2-hydroxypropyl or 2,3-hydroxypropyl esters; also ethoxylated and polyethoxylated hydroxyalkyl esters, such as esters of alcohols of the formula:

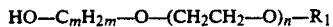

wherein $R_1$ represents hydrogen or methyl, m represents 2 to 5 and n represents 1 to 20, or esters of analogous alcohols, wherein a part of the ethyleneoxide units is replaced by propylene oxide units. Further suitable esters are dialkylaminoalkyl acrylates and methacrylates, such as the 2-(dimethylamino)-ethyl-, 2-(diethylamino)-ethyl- and 3-(dimethylamino)-2-hydroxypropyl esters. The esters can be readily saponified with caustic to the parent acids if desired. Another class of hydrophilic electrophiles are acrylamide and methacrylamide as well as amides substitutes by lower hydroxyalkyl, lower oxaalkyl- or lower dialkylaminoalkyl groups such as N-(hydroxymethyl)-acrylamide and -methacrylamide, N-(3-hydroxypropyl)-acrylamide, N-(2-hydroxyethyl)-methacrylamide, N-(1,1-dimethyl-3-oxabutyl)-acrylamide and N-(1,1-dimethyl-2-(hydroxymethyl)-3-oxabutyl)-acrylamide; methylol and ethers thereof: acrylamide, methacrylamide, diacetone acrylamide, and 2-hydroxyethyl methacrylate, as well as N-vinylpyrrolidone, acrylonitrile and methacrylonitrile.

Anionic hydrophilic activated olefins are known per se and include acrylic acid and methacrylic acid and salts thereof, acrylamidopropane sulfonic acid and salts thereof, maleic, fumaric, citraconic, muconic and itaconic acid and salts thereof as well as mono-olefinic sulfonic acids and their salts, such as sodium ethylene sulfonate, sodium styrene sulfonate and 2-acrylamido-2-methylpropane sulfonic acid.

Electrophiles which undergo nucleophilic substitution are, for example, but without limitation: halo-carboxylic acids and their derivatives such as chloro-, bromo- or iodo-acetic, butyric, decanoic, hexadecanoic, hexanoic, dodecanoic, mandelic, octanoic, pyruvic, tetradecanoic, undecanoic, pivalic, valeric, succinic, and propionic acids. Ester derivatives include methyl, ethyl, propyl, butyl, 2-hydroxyethyl, 3-hydroxypropyl, 2-hydroxypropyl or 2,3-hydroxypropyl esters; also ethoxylated and polyethoxylated hydroxyalkyl esters, such as esters of alcohols of the formula:

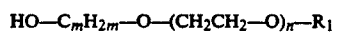

wherein $R_1$ represents hydrogen or methyl, m represents 2 to 5 and n represents 1 to 20 or esters of analogous alcohols, wherein a part of the ethylene oxide units is replaced by propylene oxide units. Further suitable esters are dialkylaminoalkyl acrylates and methacrylates, such as the 2-(dimethylamino)-ethyl-, 2-(diethylamino)-ethyl- and 3-(dimethylamino)-2-hydroxypropyl esters. The above compounds can be substituted as well, for instance; chlorophenoxyacetic, 4-chloro-o-tolyloxyacetic, and 2-(2-chlorophenoxy)-2-methylpropionic acids. These esters can be readily saponified with caustic to the parent acids if desired.

Other anionic electrophiles are known per se and include 2-chloro-ethane sulfonic acid and salts thereof, 3-chloro-2-hydroxy-1-propanesulfonic acid and salts thereof.

If one of the components (reactant or solvent) boils below the reaction temperature, the reaction is desirably carried out in a pressure tube or an autoclave. It is most preferable for economic reasons to carry out the addition reactions in that solvent from which the adduct will be applied to a substrate such as textile, paper, leather and the like or which solvent can be utilized for additional reactions to be carried out with the adduct. The addition reaction is very simple to carry out, i.e. the mercaptan, the di- or triester are dissolved at the desired molar ratios in a solvent described above and the catalyst (0.01-2%) is added. The reaction mixture is kept at a temperature ranging from room temperature to 100° C., preferably under nitrogen until the disappearance of the double bond of the ester indicates that the reaction is complete. Other means of following the reaction are GC (gas chromatography), titration of free mercapto groups or TLC (thin layer chromatography). Required reaction times depend on reaction temperatures and amounts and kind of catalysis employed and may range from 5 minutes to 24 hours. To obtain products free of coloration, it is preferred to work at reaction temperatures below 80° C., preferably 40° to 70° C. If required, the addition product can be isolated by evaporating the solvent and catalyst (low volatile catalysts such as triethylamine are preferred) and be purified employing crystallization, precipitation or distillation procedures.

These mercapto-alcohols are characterized by the fact that they contain one pair of closely packed $R_f$ groups per SH-group. This fact is most important since closely packed $R_f$ groups have been found to yield derivatives having higher oil repellency levels if compared with analogous derivatives derived from a mercaptan containing just one $R_f$-group or $R_f$-groups which are not closely packed, but separated by one or more backbone carbons.

The mercapto-alcohols can be used directly or indirectly with electrophiles to make a variety of condensation products and examples are presented in the experimental section.

The novel adducts are useful in many ways: they can be applied to substrates such as textiles, paper, leather, wood, metallic surfaces and the like providing oil and water repellency to the treated substrates at extremely low add-ons. As shown in the examples, good repellency ratings are obtained with as little fluorine as 0.03-2% by weight of the substrate. The novel adducts may be applied to the various substrates by various coating techniques, such as dipping, spraying, brushing, padding, roll coating, and the like.

These adducts can be applied from a solvent and preferably from a solvent in which it was prepared for economical reasons. The adducts may also be applied from an aqueous system if either the adduct solution is water miscible or the adduct solution has been post-emulsified, employing emulsifiers and emulsification techniques known in the art.

Of course, it is understood that besides application to textiles, the coatings of the fluorinated compositions of the present invention are useful in providing oil and water repellent coatings for leather, paper, wood, masonry, metals, plastics, glass, painted surfaces, and the like. A very significant advantage of the compositions of the present invention is that they form effective oil repellent coatings at relatively very low fluorine levels on the substrate. In other words, on a given weight basis, the fluorine content of the compositions of this invention exhibits more effective repellent properties than the same level of fluorine in other compositions previously utilized in the art.

A further advantage of the compositions of this invention is that they may not require a separate curing or heating step, but can provide excellent repellent properties after drying in air.

Still another aspect of the instant invention are the polythiourethanes prepared from the instant mercapto-alcohols of formula I or II with a diisocyanate. Such polythiourethanes are represented by repeating structural units of formula VIII or IX

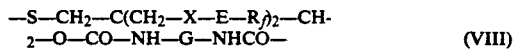
(VIII)

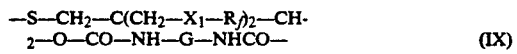
(IX)

where

X, $X_1$, E, and $R_f$ are as defined above in formula I and II and G is the residue of an aliphatic, cycloaliphatic or aromatic diisocyanate after removal of the two NCO groups.

Any convenient diisocyanate can be used to react with the $R_f$-mercapto-alcohol. Myriads of useful diisocyanates are well-known in the art. Depending on the conditions selected an equivalent amount of a diisocyanate can be reacted with the mercapto-alcohol. Thus, one can use aliphatic, cycloaliphatic or aromatic diisocyanates.

Useful aromatic diisocyanates can be represented by the formula $$G(NCO)_2$$

where G is the radical of the diisocyanate after removal of the two NCO groups.

Aromatic diisocyanates include:

tolylene diisocyanate (TDI) (all isomers), 4,4'-diphenylmethane diisocyanate (MDI), toluidine diisocyanate, dianisidine diisocyanate, m-xylylene diisocyanate, p-phenylene diisocyanate, m-phenylene diisocyanate, 1-chloro-2,4-phenylene diisocyanate, 3,3'-dimethyl-4,4'-biphenylene diisocyanate, 4,4'-bis(2-methylisocyanatophenyl)methane, 4,4'-biphenylene diisocyanate, 4,4'-bis(2-methoxyisocyanatophenyl)methane, 1-nitro-phenyl-3,5-diisocyanate, 4,4'-diisocyanatodiphenyl ether, 3,3'-dichloro-4,4'-diisocyanatodiphenyl ether, 3,3'-dichloro, 4,4'-diisocyanatodiphenylmethane, 4,4'-diisocyanatodibenzyl, 3,3'-dimethoxy-4,4'-diisocyanatodiphenyl, 2,2'-dimethyl-4,4'-diisocyanatodiphenyl, 2,2'-dichloro-5,5'-dimethoxy-4,4'-diisocyanatodiphenyl, 3,3'-dichloro-4,4'-diisocyanatodiphenyl, 1,2-naphthalene diisocyanate, 4-chloro-1,2-naphthalene diisocyanate, 4-methyl-1,2-naphthalene diisocyanate, 1,5-naphthalene diisocyanate, 1,6-naphthalene diisocyanate, 1,7-naphthalene diisocyanate, 1,8-naphthalene diisocyanate, 4-chloro-1,8-naphthalene diisocyanate, 2,3-naphthalene diisocyanate, 2,7-naphthalene diisocyanate, 1,8-dinitro-2,7-naphthalene diisocyanate, 1-methyl-2,4-naphthalene diisocyanate, 1-methyl-5,7-naphthalene diisocyanate, 6-methyl-1,3-naphthalene diisocyanate, 7-methyl-1,3-naphthalene diisocyanate, polymethylene polyphenyl isocyanate and co-products of hexamethylene diisocyanate and tolylene diisocyanate.

Useful aliphatic and cycloaliphatic diisocyanates include those of general formula $$G(NCO)_2$$

where G is the residue of the aliphatic or cycloaliphatic diisocyanate after removal of the two NCO groups.

Useful aliphatic or cycloaliphatic diisocyanates include:

1,2-ethane diisocyanate, 1,3-propane diisocyanate, 1,4-butane diisocyanate, 2-chloropropane-1,3-diisocyanate, pentamethylene diisocyanate, propylene-1,2-diisocyanate, 1,6-hexane diisocyanate, 1,8-octane diisocyanate, 1,10-decane diisocyanate, 1,12-dodecane diisocyanate, 1,16-hexadecane diisocyanate, 1,3-cyclohexane diisocyanate, 1,4-cyclohexane diisocyanate, 4,4'-methylene bis(cyclohexyl isocyanate) and isophorone diisocyanate.

Additionally, the following diisocyanates are particularly preferred because urethane compositions made therefrom tend to be non-yellowing:

1,6-hexamethylene diisocyanate (HDI), 2,2,4- and 2,4,4-trimethylhexamethylene diisocyanate (TMDI), dimer acid derived diisocyanate (DDI) obtained from dimerized fatty acids, such as linoleic acid, 4,4'-dicyclohexylmethane diisocyanate (hydrogenated MDI), isophorone diisocyanate, 3-isocyanatomethyl-3,5,5-trimethylcyclohexyl diisocyanate, lysine methyl ester diisocyanate (LDIM), bis(2-isocyanatoethyl) fumarate (FDI), bis(2-isocyanatoethyl)carbonate, m-tetramethylxylylene diisocyanate (TMXDI), The reaction between the diisocyanate and the mercapto-alcohol component can be carried out in bulk, i.e., without solvent, or in the presence of non-reactive, anhydrous, organic solvents. Solvent media in which the reaction can be carried out include ketones, such as acetone, methyl ether ketone and methyl isobutyl ketone; esters such as ethyl acetate, isopropyl acetate, butyl acetate, 2-ethylhexyl acetate; hydrocarbons such as hexane, heptane, octane and higher homologs, cyclohexane, benzene, toluene, xylene or blends of aliphatic, cycloaliphatic and aromatic hydrocarbons or aprotic solvents such as N-methylpyrrolidine; it is also possible to employ ethers, both aliphatic and alicyclic including di-n-propyl ether, di-butyl ether, tetrahydrofuran and the diethers of polyalkylene oxides. In addition, chlorinated solvents such as 1,1,1-tri-chloroethane, dichloroethyl ether, ethylene dichloride, perchloroethylene and carbon tetrachloride can be used.

Among the solvents listed, the water miscible solvents such as acetone and methyl ethyl ketone are most important since they allow conversions of $R_f$-urethanes into water soluble $R_f$-urethanes as previously described.

In all cases, the solvents should be anhydrous to avoid urea formation.

The reaction can, if desired, be catalyzed and those catalysts conventionally employed in the urethane art are useful herein. Useful catalysts fall principally in two groups a. amino compounds and other bases:

triethylamine and other trialkylamines, triethylenediamine, 1,4-diaza-2,2,2-bicyclooctane, N-(lower)alkylmorpholines, N,N,N',N'-tetra-methylethylenediamine, N,N,N',N'-tetramethyl-1,3-butanediamine, substituted piperazines, dialkylalkanolamines, benzyltrimethylammonium chloride and b. organometallic and inorganic compounds:

cobalt naphthenate, stannous chloride, stannous octoate, stannous oleate, dimethyl tin dichloride, di-n-butyltin dilaurylmercaptide, tetra-n-butyl-tin, trimethyl-tin hydroxide, di-n-butyltin dilaurate.

Such catalysts may be used singly or in combination with each other. Beneficial synergistic catalysis may occur when combinations are used.

While it is possible to carry out the reaction without the use of a catalyst, it is preferably for reasons of economy and to assure a complete reaction, to utilize one or more catalysts as listed in amounts ranging from 0.001 to 1% based on the weight of the reactants. It is similarly advantageous to carry out the urethane synthesis at elevated temperature, usually between room temperature and 120° C., preferably at 60° C. to 80° C., to obtain a complete reaction between 0.5 to 8 hours reaction time.

The reaction can be easily followed by titration of the isocyanate group or by IR analysis.

These end products include low molecular weight polythiourethane compositions useful to render plastics soil repellent, and high molecular weight compositions useful as elastomers, foams, paints and varnishes, and textile treating compositions. The polythiourethanes are readily obtained by reaction of the said mercapto-alcohols with a variety of diisocyanates as described above.

These compositions have extremely low free surface energies and therefore, possess oil and water repellent properties, as well as mold release and other properties associated with low free surface energy. It should be noted that the compositions of this invention are characterized by the presence of two perfluoroalkylhetero groups in close proximity, a characteristic which provides improved oil and water repellent properties over the fluorinated compositions of the prior art. Further the two perfluoroalkylthio groups are connected via a neopentyl moiety which does not permit the thermal elimination of mercaptan by beta-elimination. Hence, these $R_f$-mercapto-alcohols and derivatives have enhanced thermal stability.

Using the $R_f$-compounds and compositions described herein, it is possible to manufacture molds that display the excellent release properties characteristic of silicone oligomers. It is also possible to prepare polymeric urethane compositions with enhanced thermal stability.

The polythiourethanes are therefore useful as ingredients in floor polishes, furniture waxers, window washing fluids, and so on. Generally, they are useful as coatings on glass, ceramics, masonry, wood, plastics, textiles, leather and metals, or as additive ingredients in such coatings.

The usefulness of the polythiourethane compositions is, conveniently shown by measuring the oil, water and soil repellency ratings of substrates such as fabrics, paper, leather, etc. which are treated with solutions or emulsions of the novel polythiourethane compositions.

Coatings of the polythiourethane compositions may be applied to any desired substrate, porous or non-porous. They are particularly suited for application to porous materials such as textiles, leather, paper, wood, masonry, unglazed porcelain and the like to provide valuable oil and water repellency properties. However, they may also be applied to non-porous materials such as metals, plastics, glass, painted surfaces and the like to provide similar oil and water repellency properties. More specifically the polythiourethane compositions of the invention act as levelling, wetting and spreading agents in formulations designed for application to floors, furniture and automobiles. In such applications a protective oil and water repellent film is left on the treated object after the removal of the bulk of the material. Such levelling, wetting, spreading and film forming properties are also useful in a. formulations for cleaning glass and other hard, non-porous materials b. hair care products such as rinses, shampoos and hair sprays.

c. paint, stain and varnish formulations for application to wood, masonry and ceramics.

In the treatment of paper the polythiourethane compositions may be present as an ingredient in a wax, starch, casein, elastomer, or wet strength resin formulation. Aqueous emulsions of the polythiourethane compositions are especially useful in the treatment of paper. By mixing the polythiourethane compositions in an aqueous or oil type paint formulation, it may be applied effectively to unpainted siding, wood, metal and masonry. In the treatment of floors and tile surfaces and like substrates, the polythiourethane compositions may be applied by their incorporation in an emulsion or solution.

Because of the ability of the surfaces treated with these polythiourethane compositions to withstand abrasive action, the advantages incident to the repellency to oil and water and their resistance to soiling imparted by coating them with the polythiourethane compositions of this invention, preferred classes of articles to be treated are papers and textiles. Illustrative papers are carbonizing tissue, wallpaper, asphalt laminates, liner board, cardboard and papers derived from synthetic fibers.

Examples 1 to 6 and 8 to 22 illustrate the preparation of the $R_f$-mercapto-alcohols and derivatives.

Examples 7, 25 and 26 illustrate the preparation of compositions, and certain utilities of these compositions.

Examples 23 and 24 demonstrate the thermal superiority of the subject mercapto-alcohols.

The following examples are presented for the purpose of illustration only and are not to be construed to limit the nature or scope of the instant invention in any manner whatsoever.

EXAMPLE 1

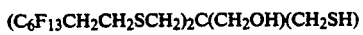

$(C_6F_{13}CH_2CH_2SCH_2)_2C(CH_2OH)(CH_2SH)$ 3,3-Bis(1,1,2,2-tetrahydroperfluorooctylthiomethyl-)oxetane (100.0 gm, 0.12 mol) and thiourea (9.2 gm, 0.12 mol) are reacted under nitrogen with sulfuric acid (12.2 gm, 0.12 mol) and 2-butanone (125 gm) as the solvent. The reaction is carried out at 80° C. for 4 hours. 2-(2-Aminoethylamino)ethanol (26.0 gm, 0.25 mol) is added over 0.5 hours. The product is stirred at 70° C. and washed once with 350 ml distilled water. Residual water is removed as an azeotrope and the remaining solvent is evaporated under vacuum. The mercapto-alcohol (92 gm, 94% of theory) is of 89% purity by GLC. The crude product is recrystallized twice from 500 gm toluene to give a final product 95% pure by GLC, m.p. 63°–65° C.

Analysis for $C_{21}H_{18}F_{26}OS_3$: Calculated: C, 28.8; H, 2.1; F, 56.4; S, 11.0. Found: C, 29.2; H, 2.0; F, 56.6; S, 10.7.

EXAMPLE 2

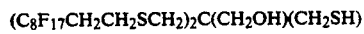

$(C_8F_{17}CH_2CH_2SCH_2)_2C(CH_2OH)(CH_2SH)$ 3,3-Bis(1,1,2,2-tetrahydroperfluorodecylthiomethyl-)oxetane (100.0 gm, 0.09 mol) and thiourea (7.3 gm, 0.10 mol) are reacted under nitrogen with sulfuric acid (9.6 gm, 0.10 mol) and 2-butanone (53.2 gm) as the solvent. The reaction is carried out at 80° C. for 4 hours. 2-(2-Aminoethylamino)ethanol (26.0 gm, 0.25 mol) is added over 0.5 hours. The product is stirred at 70° C. and washed once with 350 ml distilled water. Residual water is removed as an azeotrope and the remaining solvent is evaporated under vacuum. The mercapto-alcohol (95 gm, 94% of theory) is of 93% purity by GLC. The crude product is recrystallized twice from 500 gm toluene to give a final product 95% pure by GLC, m.p. 84°–86° C.

Analysis for $C_{25}H_{18}F_{34}OS_3$: Calculated: C, 27.9; H, 1.7; F, 60.0; S, 8.9. Found: C, 27.5; H, 1.7; F, 58.6; S, 8.3.

EXAMPLE 3

$(C_7F_{15}CONHCH_2CH_2SCH_2)_2C(CH_2OH)(CH_2SH)$

N-(2-Mercaptoethyl)-perfluorooctanamide (11.3 gm, 0.025 mol) and 3,3-bis(bromomethyl)oxetane (3.1 gm, 0.013 mol) are reacted under nitrogen with potassium carbonate (3.3 gm, 0.025 mol) and 2-pentanone (4.0 gm) as the solvent. The reaction is run at 103° C. for 19.5 hours. The reaction mixture is stirred and washed twice with distilled water. The solvent is evaporated to yield a yellow-brown wax. This product (15.0 gm, 0.016 mol) is then reacted with thiourea (1.3 gm, 0.017 mol), sulfuric acid (1.9 gm, 0.019 mol), and 2-propanol (18.2 gm) and heated to 90° C. under nitrogen for five hours. The reaction is then reacted with 2-(2-aminoethylamino)ethanol (3.1 gm, 0.030 mol) and 2-propanol (19 gm) and heated to 85° C. for fifteen minutes. The product is washed three times with distilled water and then collected. The mercapto-alcohol is of 85% purity by GLC.

EXAMPLE 4

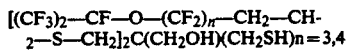

$[(CF_3)_2—CF—O—(CF_2)_n—CH_2—CH_2—S—CH_2]_2C(CH_2OH)(CH_2SH) \ n=3,4$

1-Heptafluoroisopropoxy-1,1,2,2-tetrahydroperfluoro-alkanethiol (consisting of 73% n=3 homolog and 27% n=4 homolog) (3.7 gm, 0.009 mol) and 3,3-bis(bromomethyl)oxetane (1.1 gm, 0.005 mol) are reacted under nitrogen with sodium hydroxide (3 mL of a 20% (w/w) aqueous solution). The reaction is carried out at 80° C. for 3 hours. The product is a brown wax and is 87% pure by GLC. This material is then washed with water. The above oxetane is then reacted with thiourea (0.2 gm, 0.003 mol), sulfuric acid (0.3 gm, 0.003 mol), and 2-propanol (3.2 gm) as described in Example 1. The reaction is heated to 80° C. for five hours under nitrogen. The product is a light-tan solid wax. This material is then reacted with 2-(2-aminoethylamino)ethanol (0.5 gm, 0.005 mol), and 2-propanol (3 gm). The reaction is heated for 15 minutes at 85° C. The product is a brown solid. The reaction is then washed with distilled water and the product is collected.

Analysis for product (n=3,4): Calculated: C, 27.6; H, 1.9; F, 55.0; S, 10.3. Found: C, 27.1; H, 1.4; F, 56.3; S, 9.3.

EXAMPLE 5

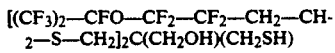

$[(CF_3)_2—CFO—CF_2—CF_2—CH_2—CH_2—S—CH_2]_2C(CH_2OH)(CH_2SH)$

4-Heptafluoroisopropoxy-1,1,2,2-tetrahydroperfluorobutanethiol (5.0 gm, 0.014 mol) and 3,3-bis(bromomethyl)oxetane (1.6 gm, 0.007 mol) are reacted under nitrogen with sodium hydroxide (4.7 ml of a 20% (w/w) aqueous solution). The reaction is carried out at 90° C. for 3 hours. The product is a clear yellow oil which is 97% pure by GC. This material is then washed with water. The oxetane is then reacted with thiourea (0.3 gm, 0.004 mol), sulfuric acid (0.4 gm, 0.004 mol), and 2-propanol (3.4 gm) as described in Example 1. The reaction is heated to 90° C. for five hours under nitrogen. The product is a brown solid wax. The isothiouronium salt is then treated with 2-(2-aminoethylamino)ethanol (0.73 gm, 0.007 mol) and 2-propanol (4 gm). The reaction is heated to 85° C. for fifteen minutes. The product is then washed three times with distilled water and collected.

EXAMPLE 6

Reaction Product of $(R_fCH_2CH_2SCH_2)_2C(CH_2OH)(CH_2SH)$ and Maleic Acid

$(R_fCH_2CH_2SCH_2)_2C(CH_2OH)CH_2SCH(COOH)CH_2COOH$ 2,2-Bis-(1,1,2,2-tetrahydroperfluoroalkylthiomethyl)-propan-3-mercapto-1-ol* (1.0 g, 0.9 mmol), ditriethanolammonium maleate (0.4 g, 0.9 mmol), and Triton B (30 μL of a 40% solution in methanol) are dissolved in 5 mL of tert-butyl alcohol in a single neck 100 mL round bottomed flask. The mixture is stirred at 50° C. for 1.5 hour under nitrogen. The yellow solution which is formed dissolved easily in distilled water. The aqueous layer is acidified and extracted with methyl propyl ketone. The solvent is removed under vacuum and the resultant yellow oil is precipitated into water to produce a white solid. NMR shows proton resonances at 2.5 ppm ($4 \times R_f CH_2$); 2.6–3.0 ppm ($10 \times SCH_2$; $2 \times CH_2CO_2$); 3.51 ($2 \times CH_2OH$); 3.72 ($1 \times SCHCO_2$).

Analysis for *$R_f$ distribution $C_6F_{13}/C_8F_{17}$-9%/88%: Calculated: C, 29.0; H, 1.9; F, 53.3; S, 8.1. Found: C, 28.9; H, 1.7; F, 53.9; S, 8.2.

This material is formulated as the ditriethanolammonium salt in aqueous solution and evaluated for paper sizing as descibed below.

Sample Preparation and Testing

Pad Application of Fluorochemicals as an External Size

A sample of the above fluorochemical is diluted to the test application levels with distilled water. The solution is added to a 4% aqueous solution of papermaker's starch and then applied to unsized paper by padding (paper dipped through starch solution, and passed through single nip rollers). The resulting sheets are dried on a hot metal surface (Williams sheet drier) 30 seconds both sides at 110° C.

Grease Resistance Test

Creased test papers are placed over a grid sheet imprinted with 100 squares. Five grams of sand are placed in the center of the crease. A mixture of synthetic oil and a dye for visualization is pipetted onto the sand and the samples are maintained at 60° C. for 24 hours. Evaluation is determined by the percentage of the grid that stains.

Another aspect of this invention describes the substrate containing 0.005 to 5% by weight of a fluorine-containing composition, at least part of said fluorine being provided by one or more units derived from the subject $R_f$-chemicals.

Oil Resistance Test TAPPI UM 557

Samples of the fluorochemical product described in Example 6 are dissolved in water as a 20% (w/w) solution and are added to a 10% aqueous solution of papermaker's starch (pH adjusted to 9.6 with 10% aq. NaOH). This starch solution is applied to unsized paper by padding (paper dipped through starch solution, then passed through single nip rollers). The resulting sheets of paper are dried at ambient conditions for 15 minutes, then for 3 minutes at 200° C. in an "Emerson Speed Drier" (heated metal plate with canvas cover).

An easily made kit of twelve solutions of varying proportions of Castor Oil, Toluene, and Heptane is useful in comparing surface oil resistance.

| Kit No. | Volume Castor Oil | Volume Toluene | Volume Heptane |
|---|---|---|---|
| 1 | 200 | 0 | 0 |
| 2 | 180 | 10 | 10 |
| 3 | 160 | 20 | 20 |
| 4 | 140 | 30 | 30 |
| 5 | 120 | 40 | 40 |
| 6 | 100 | 50 | 50 |
| 7 | 80 | 60 | 60 |
| 8 | 60 | 70 | 70 |
| 9 | 40 | 80 | 80 |
| 10 | 20 | 90 | 90 |
| 11 | 0 | 100 | 100 |
| 12 | 0 | 90 | 110 |

The "kit value" is defined as the highest number solution that will stand on the surface of the plate for 15 seconds in the form of drops without failing. Failure is detected by pronounced darkening caused by penetration. The darkening of even a small fraction of the area under the drop is considered failure.

The AATCC Oil Rating is determined according to Standard Test method 118-1983 of the American Association of Textile Chemists and Colorists. Ratings are given from 0 (minimum) to 8 (maximum). A commonly accepted level of repellency for oil repellent fabrics in the United States is an oil repellency of 4.

Tests are run against the competitive commerical paper size—SCOTCHBAN FC-807 (3M Co.), a bis-perfluoroalkyl phosphate ester, ammonium salt. The products are applied to paper by pad application and tested for Oil Kit Rating and the Grease Resistance Test.

| Test Compound | % Fluorine (Found). on Wt. of Paper | Oil Kit Number | Grease Resistance Test |
|---|---|---|---|
| Example 6 | 0.036 | 3 | fail |
|  | 0.042 | 4 | pass |
| SCOTCHBAN | 0.060 | 6 | fail |
| FC-807 | 0.066 | 7 | pass |

The results show that Example 6 has superior performance compared to that of the prior-art phosphate size, at much lower application levels, as measured by the Grease Resistance Test. Further, the novel instant carboxylate compound of Example 6 passes the Grease Resistance Test at lower Kit Numbers. This allows their application to products requiring better adhesive bonding, better label adhesion, and lessens problems with printing.

EXAMPLE 7

$(R_f CH_2CH_2SCH_2)_2C(CH_2OH)(CH_2SH)$ 3,3-Bis(1,1,2,2-tetrahydroperfluoroalkylthiomethyl-)oxetane* (described in Example 1 of copending application Ser. No. 444,073) is reacted with thiourea and sulfuric acid in 2-butanone as described in Example 1. The resultant isothiouronium salt is cleaved with 2-(2-aminoethylamino)ethanol to yield the desired mercapto-alcohol. The mercapto-alcohol is of 92% purity by GLC. m.p. 71°–78° C.

*$R_f$-distribution is $C_6$, $C_8$, $C_{10}$, $C_{12}$, $C_{14}$(%)-9/88/1.2/0.3/0.1

Calculated: C, 28.0; H, 1.7; F, 59.0; S, 9.0. Found: C, 27.6; H, 1.7; F, 57.4; S, 8.2.

EXAMPLE 8

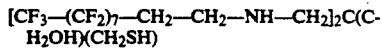

$[CF_3-(CF_2)_7-CH_2-CH_2-NH-CH_2]_2C(CH_2OH)(CH_2SH)$ 3,3-Bis(bromomethyl)oxetane is reacted with 1,1,2,2-tetrahydroperfluorodecylamine in triethylamine as solvent at 80°–100° C. The reaction is carried out for 12 hours and the product is worked up by acidification and precipitation into water. The powder is collected by filtration and dried. The oxetane is then treated with thiourea and sulfuric acid in tert-butanol and subsequently cleaved with 2-(2-aminoethylamino)ethanol as described in Example 1 to yield 2,2-bis-(1,1,2,2-tetrahydroperfluorodecyliminomethyl)-1,3-mercaptopropanol.

EXAMPLE 9

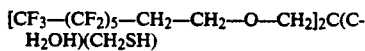

3,3-Bis(1,1,2,2-tetrahydroperfluorooctyloxomethyl)oxetane (described in copending application Ser. No. 444,073) is treated with thiourea and sulfuric acid in tert-butanol and subsequently cleaved with 2-(2-aminoethylamino)ethanol as described in Example 1 to yield 2,2-bis-(1,1,2,2-tetrahydroperfluorooctyloxamethyl)-1,3-mercaptopropanol.

EXAMPLE 10

3,3-Bis(N-ethylperfluorooctanesulfonamidomethyl)oxetane (described in copending application Ser. No. 444,073) is treated with thiourea and sulfuric acid in tert-butanol and subsequently cleaved with 2-(2-aminoethylamino)ethanol as described in Example 1 to yield 2,2-bis(N-ethylperfluorooctanesulfonamidomethyl)-1,3-mercaptopropanol.

EXAMPLES 11 TO 19

Using the general methods described in Examples 1–10, the following additional mercapto-alcohols are prepared.

| Ex. | Fluorochemical | Mercapto-Alcohol |
|---|---|---|
| 11 | $CF_3CF_2CH_2SH$ | $(CF_3CF_2CH_2SCH_2)_2C(CH_2OH)(CH_2SH)$ |
| 12 | $C_6F_{13}(CH_2)_4SH$ | $(C_6F_{13}(CH_2)_4SO_2CH_2)_2C(CH_2OH)(CH_2SH)$ |
| 13 | $C_8F_{17}CH_2CH_2CH_2SH$ | $(C_8F_{17}CH_2CH_2CH_2SCH_2)_2C(CH_2OH)(CH_2SH)$ |
| 14 | $C_8F_{17}CH_2CH_2N(CH_3)CH_2CH_2CH_2SH$ | $(C_8F_{17}CH_2CH_2N(CH_3)CH_2CH_2CH_2SCH_2)_2C(CH_2OH)(CH_2SH)$ |
| 15 | $C_8F_{17}SO_2NHCH_2CH_2SH$ | $(C_8F_{17}SO_2NHCH_2CH_2SCH_2)_2C(CH_2OH)(CH_2SH)$ |
| 16 | $C_8F_{17}CH_2CH_2SO_2NHCH_2CH_2SH$ | $(C_8F_{17}CH_2CH_2SO_2NHCH_2CH_2SCH_2)_2C(CH_2OH)(CH_2SH)$ |
| 17 | $C_7F_{15}CONHCH_2CH_2S$ | $(C_7F_{15}CONHCH_2CH_2SCH_2)_2C(CH_2OH)(CH_2SH)$ |
| 18 | $C_8F_{17}CH_2CH_2OH$ | $(C_8F_{17}CH_2CH_2OCH_2)_2C(CH_2OH)(CH_2SH)$ |
| 19 | $C_6F_{13}CH_2CH_2OH$ | $(C_6F_{13}CH_2CH_2OCH_2)_2C(CH_2OH)(CH_2SH)$ |

EXAMPLES 20-21

Stability of Bis-perfluoroalkylmercapto-alcohol Derivatives

Thermogravimetric analyses are run on the mercapto-alcohol of Example 7 and the maleic acid derivative of Example 6. The instrument is run at 10° C./minute to either 350° C. or 500° C. with 100 ml/min $N_2$ or in air.

| Cmpd of | TGA (Wt. Loss) Temperature (°C.) of Indicated Weight Loss | | | | | | |
|---|---|---|---|---|---|---|---|
| | | Under Nitrogen | | | Under Air | | |
| Example | DSC (Tm) | Init. | 10% | 50% | Init. | 10% | 50% |
| 7 | 165-1 | 215 | 286 | 349 | 175 | 255 | 306 |
| 6 | 28-34 | 75 | 261 | 315 | 71 | 250 | 301 |

These results indicate the thermal superiority of the subject bis-perfluoroalkylthio-neopentyl type mercapto alcohols and their derivatives. The subject mercapto-alcohol and derivative as exemplified above both are appreciably stable to a temperature greater than 280° C. in nitrogen, even to 260° C. in air.

EXAMPLE 22

The mercapto-alcohol of Example 7 is predried azeotropically with isopropyl acetate or with 1,1,1-trichloroethane. An equimolar amount of the dried mercapto-alcohol is then reacted with an equimolar amount of isophorone diisocyanate under nitrogen in the presence of a catalytic amount of triethylamine and dibutyltin dilaurate with isopropyl acetate as solvent. The reaction mixture is heated at reflux for two hours and the completeness of the reaction is indicated by the absence of the N=C=O infrared band at 2270 cm$^{-1}$.

EXAMPLE 23

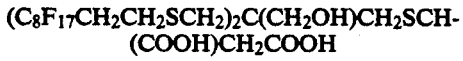

2,2-Bis(1,1,2,2-tetrahydroperfluorodecylthiomethyl)-3-bromo-1-propanol (17.4 g, 16.6 mmol; prepared from the corresponding oxetane using hydrobromic acid and described in Example 9 of copending application Ser. No. 620,232), diethyl mercaptosuccinate (6.5 g, 31 mmol), potassium carbonate (4.3 g, 31 mmol) and acetone (50 ml) is charged to a three-necked flask and heated at reflux overnight. Water is added and the mixture is extracted three times with methyl propyl ketone. The product is purified by silica gel chromatography to yield a yellow oil which is 99% pure by GLC.

The above diethyl ester (9.5 g, 7.6 mmol) is dissolved in 20 l of diglyme and water (3 ml) in a single neck flask. Sodium hydroxide (1.5 ml of a 50% aqueous solution) is added and the mixture allowed to stir overnight at room temperature. Water is added, and the mixture extracted with methyl propyl ketone. The aqueous layer is acidified and extracted with methyl propylketone. The solvent is removed under vacuum and the resultant yellow oil is precipitated into water to produce a white solid. NMR shows proton resonances at 2.5 ppm (4×R$_f$CH$_2$); 2.6–3.0 ppm (10×SCH$_2$); 3.51 ppm (2×CH$_2$OH); 3.72 ppm (1×SCHCOO).

Analysis for $C_{29}H_{22}F_{34}S_3O_5$: Calculated: C, 29.2; H, 1.8; F, 54.1; S, 8.1. Found: C, 28.9; H, 1.7; F, 53.9; S, 8.2.

EXAMPLE 24

2,2-Bis(1,1,2,2-tetrahydroperfluorodecylthiomethyl)-1,3-dibromopropane (25 g, 21 mmol, prepared from the bromopropanol cited in Example 23 using phosphorus tribromide and described in Example 11 of copending application Ser. No. 620,232), ethyl 2-mercaptoacetate (5.1 g, 41 mmol), potassium carbonate (5.8 g, 42 mmol) and acetone (70 ml) is reacted and the product purified as described in Example 23. The resultant diester is saponified, acidified and precipitated into water to yield the above-identified diacid as a white powder.

What is claimed is:

1. A linear polythiourethane having recurring structural units of formula VIII or IX

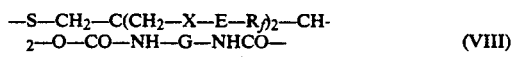

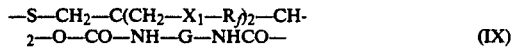

where

R_f is a straight or branched chain perfluoroalkyl of 1 to 18 carbon atoms or said perfluoroalkyl substituted by perfluoroalkoxy of 2 to 6 carbon atoms, E is branched or straight chain alkylene of 1 to 10 carbon atoms or said alkylene interrupted by one to three groups selected from the group consisting of —NR—, —O—, —S—, SO$_2$—, —COO—, —OOC—, —CONR—, —NRCO—, —SO$_2$NR—, and —NRSO$_2$—, or terminated at the R_f end with —CONR— or —SO$_2$NR—, where R_f is attached to the carbon or sulfur atom, X is —S—, —O—, —SO$_2$—, or —NR—, X$_1$ is —CONR— or —SO$_2$NR—, where R_f is attached to the carbon or sulfur atom, R is independently hydrogen, alkyl of 1 to 6 carbon atoms or hydroxyalkyl of 2 to 6 carbon atoms, and G is the radical of an aliphatic, cycloaliphatic or aromatic diisocyanate after removal of the two NCO groups.

2. A polythiourethane according to claim 1 wherein R_f is perfluoroalkyl of 4 to 18 carbon atoms or perfluoroalkyl of 2 to 6 carbon atoms substituted by perfluoroalkoxy of 2 to 6 carbon atoms.

3. A polythiourethane according to claim 1 where in the compound of formula VIII, R_f is perfluoroalkyl of 6 to 16 carbon atoms or perfluoroalkyl of 2 to 6 carbon atoms substituted by perfluoroalkoxy of 2 to 6 carbon atoms, E is alkylene of 2 to 6 carbon atoms, —CONHCH$_2$CH$_2$—, —CH$_2$CH$_2$N(CH$_3$)CH$_2$CH$_2$—, —CH$_2$CH$_2$SO$_2$NHCH$_2$CH$_2$—, —CH$_2$CH$_2$OCH$_2$CH$_2$—, or —SO$_2$NHCH$_2$CH$_2$—, and X is —S—, —SO$_2$— or —O—.

4. A polythiourethane according to claim 1 where in the compound of formula VIII, R_f is perfluoroalkyl of 6 to 14 carbon atoms, E is ethylene, and X is —S—.

5. A polyurethane according to claim 1 wherein G is the radical of a diisocyanate selected from the group consisting of tolylene diisocyanate (TDI) (all isomers), 4,4'-diphenylmethane diisocyanate (MDI), toluidine diisocyanate, dianisidine diisocyanate, m-xylylene diisocyanate, p-phenylene diisocyanate, m-phenylene diisocyanate, 1-chloro-2,4-phenylene diisocyanate, 3,3'-dimethyl-4,4'-bisphenylene diisocyanate, 4,4'-bis(2-methylisocyanatophenyl)methane, 4,4'-bisphenylene diisocyanate, 4,4'-bis(2-methoxyisocyanatophenyl)methane, 1-nitro-phenyl-3,5-diisocyanate, 4,4'-diisocyanatodiphenyl ether, 3,3'-dichloro-4,4'-diisocyanatodiphenyl ether, 3,3'-dichloro,4,4'-diisocyanatodiphenyl-methane, 4,4'-diisocyanatodibenzyl, 3,3'-dimethoxy-4,4'-diisocyanatodiphenyl, 2,2'-dimethyl-4,4'-diisocyanatodiphenyl, 2,2'-dichloro-5,5'-dimethoxy-4,4'-diisocyanatodiphenyl, 3,3'-dichloro-4,4'-diisocyanatodiphenyl, 1,2-naphthalene diisocyanate, 4-chloro-1,2-naphthalene diisocyanate, 4methyl-1,2-naphthalene diisocyanate, 1,5-naphthalene diisocyanate, 1,6-naphthalene diisocyanate, 1,7-naphthalene diisocyanate, 1,8-naphthalene diisocyanate, 4-chloro-1,8-naphthalene diisocyanate, 2,3-naphthalene diisocyanate, 2,7-naphthalene diisocyanate, 1,8-dinitro-2,7-naphthalene diisocyanate, 1-methyl-2,4-naphthalene diisocyanate, 1-methyl-5,7-naphthalene diisocyanate, 6-methyl-1,3-naphthalene diisocyanate, 7-methyl-1,3-naphthalene diisocyanate, polymethylene polyphenyl isocyanate and co-products of hexamethylene diisocyanate and tolylene diisocyanate, 1,2-ethane diisocyanate, 1,3-propane diisocyanate, 1,4-butane diisocyanate, 2-chloropropane-1,3-diisocyanate, pentamethylene diisocyanate, propylene-1,2-diisocyanate, 1,6-hexane diisocyanate, 1,8-octane diisocyanate, 1,10-decane diisocyanate, 1,12-dodecane diisocyanate, 1,16-hexadecane diisocyanate, 1,3-cyclohexane diisocyanate, 1,4-cyclohexane diisocyanate, 4,4'-methylene bis(cyclohexyl isocyanate), 1,6-hexamethylene diisocyanate (HDI), 2,2,4- and 2,4,4-trimethylhexamethylene diisocyanate (TMDI), dimer acid derived diisocyanate (DDI) obtained from dimerized fatty acid, 4,4'-dicyclohexylmethane diisocyanate (hydrogenated MDI), isophorone diisocyanate (=3-isocyanatomethyl-3,5,5-trimethylcyclohexyl isocyanate), lysine methyl ester diisocyanate (LDIM), bis(2-isocyanatoethyl) fumarate (FDI), bis(2-isocyanatoethyl) carbonate and m-tetramethylxylylene diisocyanate (TMXDI).

6. A polythiourethane according to claim 1 wherein G is a radical of a diisocyanate selected from the group consisting of 1,6-hexamethylene diisocyanate (HDI), 2,2,4- and 2,4,4-trimethylhexamethylene diisocyanate (TMDI), dimer acid derived diisocyanate (DDI) obtained from dimerized fatty acid, 4,4'-dicyclohexylmethane diisocyanate (hydrogenated MDI), isophorone diisocyanate (=3-isocyanatomethyl-3,5,5-trimethylcyclohexyl isocyanate), lysine methyl ester diisocyanate (LDIM), bis(2-isocyanatoethyl) fumarate (FDI), bis(2-isocyanatoethyl) carbonate and m-tetramethylxylylene diisocyanate (TMXDI).

7. A polythiourethane according to claim 1 having recurring structural units of formula VIII where R_f is a mixture of C$_6$F$_{13}$, C$_8$F$_{17}$, C$_{10}$F$_{21}$, C$_{12}$F$_{25}$ and C$_{14}$F$_{29}$, E is ethylene, X is —S— and G is a radical of isophorone diisocyanate after removal of two NCO groups.

* * * * *